(12) United States Patent
McGlamery, Jr. et al.

(10) Patent No.: US 7,893,310 B2
(45) Date of Patent: *Feb. 22, 2011

(54) METHOD OF SEPARATING CONDENSED LIQUID FROM AN OLEFIN STREAM

(75) Inventors: Gerald G. McGlamery, Jr., Houston, TX (US); Michael P. Nicoletti, Houston, TX (US); Thomas H. Colle, Houston, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 495 days.

This patent is subject to a terminal disclaimer.

(21) Appl. No.: 12/023,459

(22) Filed: Jan. 31, 2008

(65) Prior Publication Data

US 2008/0188700 A1    Aug. 7, 2008

Related U.S. Application Data

(63) Continuation-in-part of application No. 11/702,345, filed on Feb. 5, 2007, now Pat. No. 7,741,528.

(51) Int. Cl.
*C07C 1/00* (2006.01)
*C07C 7/10* (2006.01)

(52) U.S. Cl. .................. 585/639; 585/638; 585/640; 585/804; 585/833; 502/214; 210/639

(58) Field of Classification Search ................. 585/638, 585/639, 640, 804, 833; 502/214; 210/639
See application file for complete search history.

(56) References Cited

U.S. PATENT DOCUMENTS 3,250,117 A * 5/1966 Dajani ...................... 73/61.62

| | | |
|---|---|---|
| 6,121,504 A | 9/2000 | Kuechler et al. |
| 6,403,854 B1 | 6/2002 | Miller et al. |
| 6,459,009 B1 | 10/2002 | Miller et al. |
| 6,482,998 B1 | 11/2002 | Kuechler et al. |
| 2004/0267068 A1 | 12/2004 | Ding et al. |
| 2004/0267069 A1 | 12/2004 | Ding et al. |

(Continued)

FOREIGN PATENT DOCUMENTS

WO    WO 03/104170    12/2003

OTHER PUBLICATIONS

Dukhin, A.S., et al. "*Electroacoustics for Concentrated Dispersions*," Dispersion Technology, Inc., pp. 1-20 [online], [retrieved on Dec. 1, 2006]. Retrieved from the Internet <http://www.dispersion.com/pages/newsletter/articles/Newsletter2.html>.

(Continued)

*Primary Examiner*—Prem C. Singh
(74) *Attorney, Agent, or Firm*—Kevin M. Faulkner; David M. Weisberg (57) ABSTRACT

This invention is to a process for separating condensed water and entrained solids from an olefin stream so that fouling of the separation equipment by the entrained solids is reduced or eliminated. The process involves injecting an antifouling agent into a water condensing or quench system in an amount to maintain a zeta potential of fouling liquid and a zeta potential of the surface of the quench system both in a positive range or both in a negative range.

6 Claims, 4 Drawing Sheets

U.S. PATENT DOCUMENTS

| | | |
|---|---|---|
| 2004/0267075 A1 | 12/2004 | Lumgair et al. |
| 2004/0267077 A1 | 12/2004 | Ding et al. |
| 2005/0137080 A1* | 6/2005 | Chang et al. .............. 502/214 |
| 2005/0234281 A1 | 10/2005 | Bjorklund et al. |
| 2006/0149111 A1 | 7/2006 | Van Egmond et al. |

OTHER PUBLICATIONS

"*Electroacoustic Theory*" (extraction from Chap. 5, [52]). Dispersion Technology, Inc., pp. 1-14 [on-line], [retrieved on Dec. 1, 2006]. Retrieved from the Internet <http://www.dispersion.com/pages/theory/electroacoustictheory/electroacoustictheory.html>.

"*Electrophoresis*", Kirk-Othmer Encyclopedia of Chemical Technology, Fourth Ed., vol. 9, pp. 356-360, John Wiley & Sons, J. I. Kroschwitz, ed. (1991).

"*Flotation*", Kirk-Othmer Encyclopedia of Chemical Technology, Fourth Ed., vol. 11, pp. 87-92, John Wiley & Sons, J. I. Kroschwitz, ed. (1991).

\* cited by examiner

METHOD OF SEPARATING CONDENSED LIQUID FROM AN OLEFIN STREAM

CROSS-REFERENCE TO RELATED APPLICATIONS

This application claims priority as a continuation-in-part of U.S. Ser. No. 11/702,345, filed Feb. 5, 2007, now U.S. Pat. No. 7,741,528, the entire contents of which are hereby incorporated by reference herein.

FIELD OF THE INVENTION

This invention relates to a method for separating condensed water and entrained solids from an olefin stream. In particular, this invention relates to a method for forming and separating an olefin fraction from an olefin stream prepared by contacting oxygenate with a zeolitic aluminosilicate molecular sieve catalyst to form the olefin stream.

BACKGROUND OF THE INVENTION

Olefins are traditionally produced from petroleum feedstock by catalytic or steam cracking processes. These cracking processes, especially steam cracking, produce olefins such as ethylene and/or propylene from a variety of hydrocarbon feedstocks. Ethylene and propylene are important commodity petrochemicals useful in many processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide.

The petrochemical industry has known for some time that oxygenates, especially alcohols, are convertible into light olefins. This process is referred to as the oxygenate-to-olefin, or OTO, process. Typically, the preferred oxygenate for light olefin production is methanol. The process of converting methanol to olefins is called the methanol-to-olefins, or MTO, process.

There are numerous technologies available for producing oxygenates, and particularly methanol, including fermentation or reaction of synthesis gas derived from natural gas, petroleum liquids, carbonaceous materials including coal, recycled plastics, municipal waste or any other organic material. The most common process for producing methanol is a two-step process of converting natural gas to synthesis gas. Then, synthesis gas is converted to methanol.

Generally, the production of synthesis gas involves a combustion reaction of natural gas, mostly methane, and an oxygen source into hydrogen, carbon monoxide and/or carbon dioxide. Synthesis gas production processes are well known, and include conventional steam reforming, autothermal reforming or a combination thereof.

Synthesis gas is then processed into methanol. Specifically, the components of synthesis gas (i.e., hydrogen, carbon monoxide and/or carbon dioxide) are catalytically reacted in a methanol reactor in the presence of a heterogeneous catalyst. For example, in one process, methanol is produced using a copper/zinc oxide catalyst in a water-cooled tubular methanol reactor.

The methanol is then converted to olefin product in a methanol-to-olefins process. The methanol-to-olefins reaction is highly exothermic and produces a large amount of water. Water comprises about half of the total weight of the output stream of the reactor or effluent stream. Consequently, the water must be removed by condensation to isolate the olefin product. The use of a quench device is one way to do this.

The effluent stream of an oxygenate-to-olefin reactor also contains byproducts including oxygenate byproducts such as organic acids, aldehydes, higher alcohols, and/or ketones. Carbon dioxide is also a byproduct of the oxygenate-to-olefin reaction. Furthermore, depending upon operating conditions, unreacted methanol is likely to be present in the effluent of the oxygenate-to-olefin reaction. Also, catalyst fines or particles may be present in the effluent of the oxygenates-to-olefins reaction.

Fouling within the quench process itself results in a decrease in efficiency of the overall oxygenates-to-olefins process and the quench process. Mitigation of the fouling would increase the efficiency of the process, allowing greater time intervals between shut downs. Further, partial neutralization of the organic acids and reduction of corrosion of the equipment are desirable.

U.S. Pat. Nos. 6,482,998 and 6,121,504 describe an oxygenate-to-olefin process that includes a quench tower for removal of water produced in the oxygenate-to-olefin reactor. Unreacted oxygenate feed (typically methanol) that is liquid under quenching conditions is removed from the quench tower as a heavy product fraction. The unreacted oxygenate feed is separated from water in the quench medium in a fractionation tower.

U.S. Pat. No. 6,403,854 and International Publication No. WO 03/104170 A1 describe a two-stage solids wash and quench for use with the oxygenate conversion process where catalyst fines are removed from the effluent stream through a first quench stage. The bottoms of the quench device include water, alcohols, ketones, and neutralized organic acids that have a boiling point greater than water. The quench medium is a portion of the quench bottoms that is mixed with a neutralization stream and purified water stream. Therefore acids such as formic acid, acetic acid, butyric acid, and propanoic acid can be neutralized. The neutralization material can be caustic, amines or ammonia.

U.S. Pat. No. 6,459,009 describes a two-stage quench tower process for removing impurities from a superheated reactor effluent stream withdrawn from an oxygenate conversion complex. The patent further describes the use of a neutralization material to neutralize any organic acid present in the effluent stream.

U.S. Patent Application Publication No. 2005/0234281 A1 describes a process for the catalytic conversion of a feedstream containing an oxygenate to light olefins using a fluidized conversion zone and a relatively expensive fluidized catalyst containing an ELAPO molecular sieve with recovery and recycle of contaminating catalyst particles from the product effluent stream withdrawn from the conversion zone.

U.S. Patent Application Publication No. 2006/0149111 A1 describes a process for converting oxygenate to olefins from a fluidized bed reactor which comprises removal of catalyst fines from a quenched vaporous effluent by contacting with a liquid low in catalyst fines content, e.g., oxygenate feedstock, or byproduct water from the oxygenates to olefins conversion which is stripped and/or filtered. The process typically comprises: contacting a feedstock comprising oxygenate with a catalyst comprising a molecular sieve under conditions effective to produce a deactivated catalyst having carbonaceous deposits and a product comprising the olefins; separating the deactivated catalyst from the product to provide a separated vaporous product which contains catalyst fines; quenching the separated vaporous product with a liquid medium containing water and catalyst fines, in an amount sufficient for forming a light product fraction comprising light olefins and catalyst fines and a heavy product fraction comprising water, heavier hydrocarbons and catalyst fines; treating the light product fraction by contacting with a liquid substantially free of catalyst fines to provide a light product fraction having reduced catalyst fines content and a liquid fraction of increased fines content; compressing the light product fraction having reduced catalyst fines content; and recovering the light olefins from the compressed light product fraction.

Notwithstanding the improvements in technology relating to the removal of impurities from olefin streams, further improvements in separating condensed water and entrained solids from an olefin stream are desired. In particular, such systems are sought where fouling is significantly reduced or eliminated.

SUMMARY OF THE INVENTION

This invention provides the ability to separate condensed water and entrained solids from an olefin stream with a significant reduction or complete elimination of fouling. In particular, this invention provides significant fouling reduction in quench systems in oxygenate-to-olefins reaction systems.

According to one aspect of the invention, there is provided a method for forming and separating an olefin fraction. In one embodiment, the olefin fraction is provided by contacting oxygenate with zeolitic aluminosilicate molecular sieve catalyst to form an olefin stream.

The olefin stream that is provided or formed is preferably cooled in a quench system. In the quench system, a first fraction comprising olefin and a second fraction comprising condensed water and entrained catalyst fraction (i.e., a fraction that contains both condensed water and entrained solids) are formed. Preferably, the quench system is comprised of a surface structure and at least a portion of the surface structure contacts the condensed water. The entrained solids can comprise inorganic oxides, such as molecular sieve catalyst. Generally, the solids are in the form of particulates.

In one embodiment, an antifouling agent is injected into the quench system in an amount to maintain a zeta potential of the entrained catalyst in the condensed water and an effective zeta potential of the surface of the quench system contacting the condensed water both in a positive range or both in a negative range. At least a portion of the second fraction comprising the condensed water and entrained catalyst is separated from the olefin fraction.

In another embodiment, the zeta potential of the entrained catalyst in the condensed water and the effective zeta potential of the surface of the quench system contacting the condensed water both have an absolute value of at least 2 mV. Preferably, the zeta potential of the entrained catalyst in the condensed water and the effective zeta potential of the surface of the quench system contacting the condensed water are both at least +2 mV.

In one embodiment of the invention, the antifouling agent is a surface affecting agent. Preferably, the surface affecting agent includes an acid, a base or a surface modifier. In a particular embodiment, the surface affecting agent is an acid or base and the acid or base is injected into the quench system in an amount to maintain a pH in the quench system of from 4 to 6. Alternatively, the antifouling agent is injected into the quench system in an amount to maintain a pH of the condensed water and entrained catalyst fraction of less than 6 or greater than 8.

In one embodiment, the quench system comprises at least one quench vessel and a pumparound system in fluid connection with the quench vessel. In a particular embodiment, the pumparound system comprises at least one pump and at least one cooling vessel. In one embodiment, the antifouling agent can be injected into the quench vessel, the pumparound system, or both.

In one embodiment, the zeolitic aluminosilicate molecular sieve catalyst particles are comprised of alumina and silica present in a silica to alumina ($Si:Al_2$) ratio of at least about 100. In a particular embodiment, the olefin stream is provided from a unit in which oxygenate is contacted with zeolitic aluminosilicate molecular sieve catalyst to form the olefin stream.

According to another aspect of the invention, there is provided a method for forming and separating olefin, which includes a step of contacting oxygenate with zeolitic aluminosilicate molecular sieve catalyst to form an olefin stream. The olefin stream is cooled in a quench system to form a first fraction comprising olefin and a second fraction comprising condensed water and entrained catalyst.

In one embodiment, the entrained catalyst in the condensed water has a first IEP and the quench system is comprised of a surface structure in contact with the condensed water having a second IEP. Preferably, an antifouling agent is injected into the quench system in an amount to maintain the second fraction comprising condensed water and entrained catalyst at a pH value that is either (i) above the greater of the first and second IEP or (ii) below the lesser of the first and second IEP.

In yet another embodiment, the surface comprises $\gamma\text{-}Fe_2O_3$ and the second IEP is 7.9. In another, the surface comprises $Fe_3O_4$ and the second IEP is 8.2.

According to another aspect of the invention, the first IEP is in the range of from about 5.6 to about 5.9, and the second IEP is in the range of from about 7.5 to about 8.5. Preferably, the antifouling agent can comprise an acid or base and can be injected in an amount to maintain a pH of the second fraction comprising condensed water and entrained catalyst of less than 5.6. Alternatively, the antifouling agent can comprise a base and can be injected in an amount to maintain a pH of the second fraction comprising condensed water and entrained catalyst of greater than 8.5.

In another aspect of the invention the quench system is comprised of an iron oxide-containing surface structure, an acid or base is injected into the quench system in an amount to maintain a pH in the quench system of from 4 to 6, and at least a portion of the second fraction comprising condensed water and entrained catalyst is separated from the first fraction comprising olefin. The iron oxide is preferably in the form of $\gamma\text{-}Fe_2O_3$ or $Fe_3O_4$, and the quench system is preferably comprised of at least one quench vessel and a pumparound system in fluid connection with the quench vessel. The pumparound system preferably comprises at least one pump and at least one cooling vessel, and the antifouling agent can be injected into the quench vessel, the pumparound system, or both.

DETAILED DESCRIPTION OF THE INVENTION

I. Separating Condensed Water and Entrained Solids from an Olefin Stream

This invention is directed to a process for separating condensed water and entrained solids from an olefin stream so that fouling of the separation equipment by the entrained solids is reduced or eliminated. The process involves injecting an antifouling agent into a water condensing or quench system in an amount to maintain a zeta potential of fouling liquid (i.e., condensed liquid, such as water, and any entrained solids or catalyst particles) and a zeta potential of the quench system surface in the presence of the condensed liquid both in a positive range or both in a negative range.

The zeta potential of a substance is the electrical potential between the shear or slipping plane of the electrical double layer of a solid surface in a fluid and the bulk fluid surrounding the solid surface. It is a function of the surface composition, the surface geometry, and any adsorbed species on the surface. According to this invention, zeta potential is measured by forming a slurry of the substance to be measured and measuring the zeta potential using an acoustic and electroacoustic spectrometer. Preferred is the acoustic and electroacoustic spectrometer model DT-1200 from Dispersion Technology, Inc., Bedford Hills, N.Y. The method to be used in determining zeta potential according to this invention is as follows:

The instrument is first calibrated before making any zeta potential measurements. Calibrations are carried out for pH, conductivity, and zeta potential. The pH is calibrated using three pH standards having pH of 4.0, 7.0, and 10.0. Conductivity is calibrated using a 0.1 M KCl solution. Zeta potential is calibrated using 10 wt % Ludox TM-50 colloidal silica (from Sigma Aldrich Inc., St. Louis, Mo.) diluted in 0.01 M KCl solution to give −38 mV, ±1 mV. The colloidal silica has a particle size of 30 nm. The calibration standard is prepared fresh before each use.

Sample suspensions can be measured using a suspension containing typically 1.5 to 5 wt % of sample particles. For example, foulant suspensions can be made by dispersing the foulant removed from a filtration device. Depending on the state of the sample, dispersion aids might be required, such as mixing or shearing, to generate a uniform and stable suspension.

Typically, measurements are taken over a wide range of pH. This technique will lead to establishment of the isoelectric point (IEP). The pH is adjusted by either adding hydrochloric acid to lower the pH or adding potassium hydroxide to increase the pH. Addition is carried out by an auto-titrator that is controlled by the software of the DT-1200 instrument. The degree of changes in pH can be controlled by specifying the number of data points in the pH range of interest. Typically, 7 to 21 points are chosen for a pH range of 2 to 12 (approximately 0.5 pH unit per data point). During the measurement, the suspension is circulated. The circulation ensures uniform sample dispersion and mixing.

The entrained solids and catalyst particles can be whole catalyst particles or fractions thereof produced by attrition or other means. During the oxygenate-to-olefin reaction, organic matter can adsorb on the surface of the particles. Upon condensation of a liquid stream in the quench system, some of the particle composition can dissolve to produce ionic species in the condensed liquid.

According to the invention, maintaining the zeta potentials of the fouling liquid and the surface of the quench system both in the negative or both in the positive range reduces or eliminates fouling. That is, little if any solids material in the fouling liquid collects on the quench system surface.

II. Olefin Streams to be Separated from Condensable Liquids

This invention is applicable to separating olefins, particularly light olefins such as ethylene, propylene and butylene, from higher boiling point compounds. It is particularly applicable for separating olefins from olefin streams containing olefin, particularly light olefins, from water that contains solid particles, particularly solid particles such as catalyst particles.

In general, an olefin stream is provided that contains olefin, water and solid particles, where the solid particles are preferably catalyst particles. The olefin stream is cooled, preferably in a quench system, to form an olefin fraction and a condensed water and entrained solid or catalyst particle fraction.

The olefin stream can be supplied from any source. In a preferred embodiment, the olefin is obtained by contacting oxygenate with a molecular sieve catalyst. The oxygenate comprises at least one organic compound that contains at least one oxygen atom, such as aliphatic alcohols, ethers, or carbonyl compounds (aldehydes, ketones, carboxylic acids, carbonates, esters and the like). When the oxygenate is an alcohol, the alcohol preferably has from 1 to 10 carbon atoms, more preferably from 1 to 4 carbon atoms. Representative alcohols include but are not necessarily limited to lower straight- and branched-chain aliphatic alcohols and their unsaturated counterparts. Examples of suitable oxygenate compounds include, but are not limited to: methanol; ethanol; n-propanol; isopropanol; $C_4$-$C_{10}$ alcohols; methyl ethyl ether; dimethyl ether; diethyl ether; di-isopropyl ether; formaldehyde; dimethyl carbonate; dimethyl ketone; acetic acid; and mixtures thereof. Preferred oxygenate compounds are methanol, ethanol, dimethyl ether, or a mixture thereof.

Molecular sieves capable of converting an oxygenate to an olefin compound include zeolites as well as non-zeolites, and are of the large-, medium- or small-pore type. Small-pore molecular sieves are preferred in one embodiment of this invention, however. As defined herein, small-pore molecular sieves have a pore size of less than or equal to about 5.0 angstroms. Generally, suitable catalysts have a pore size ranging from about 3.5 to about 5.0 angstroms, preferably from about 3.5 to about 4.8 angstroms, and most preferably from about 3.5 to about 4.6 angstroms.

Zeolites include materials containing silica and optionally alumina, and materials in which the silica and alumina portions have been replaced in whole or in part with other oxides.

For example, germanium oxide, tin oxide, and mixtures thereof can replace the silica portion. Boron oxide, iron oxide, gallium oxide, indium oxide, and mixtures thereof can replace the alumina portion. Unless otherwise specified, the terms "zeolite" and "zeolite material" as used herein, shall mean not only materials containing silicon atoms and, optionally, aluminum atoms in the crystalline lattice structure thereof, but also materials which contain suitable replacement atoms for such silicon and aluminum atoms.

Conventional crystalline aluminosilicate zeolites having catalytic activity are desirable molecular sieves that can be used in making the catalyst of this invention. Non-limiting examples of zeolites which can be employed in the practice of this invention, include both natural and synthetic zeolites. These zeolites include zeolites of the structural types included in the *Atlas of Zeolite Framework Types*, edited by Ch. Baerlocher, W. M. Meier, D. H. Olson, Fifth Revised edition, Elsevier, Amsterdam, 2001. In one embodiment, the crystalline aluminosilicate molecular sieve can have a silica to alumina molar ratio from about 20 to about 400, for example from about 20 to about 150, from about 20 to about 100, from about 45 to about 90, from about 80 to about 350, from about 100 to about 300, from about 50 to about 200, or from about 75 to about 275.

In one preferred embodiment, the molecular sieve catalyst composition comprises an aluminosilicate catalyst composition, preferably a relatively high-silica aluminosilicate catalyst composition. Relatively high-silica aluminosilicates, as used herein, can advantageously include those having a molar relationship of $X_2O_3:(n)YO_2$ (wherein X is a trivalent element and Y is a tetravalent element), in which n is at least about 80, preferably at least about 100, for example at least about 120, at least about 150, at least about 180, or at least about 200, and typically not more than about 5000, preferably not more than about 4000, for example not more than about 3500, not more than about 3000, not more than about 2500, or not more than about 2000. Alternatively, n for relatively high-silica aluminosilicates can be from about 300 to about 4000, for example from about 300 to about 2500.

Non-limiting examples of trivalent X can include aluminum, boron, iron, indium, gallium, and combinations thereof, preferably at least including aluminum. Non-limiting examples of tetravalent Y can include silicon, tin, titanium, germanium, and combinations thereof, preferably at least containing silicon.

In embodiments where X represents aluminum and Y represents silicon, the factor n represents a silica:alumina ratio, also termed $Si:Al_2$. Another measure of relative proportion in such cases is the ratio of Y:X, or the silicon:aluminum ratio. In one embodiment, the silicon:aluminum (Si:Al) ratio of the aluminosilicates can be at least about 40, preferably at least about 50, for example at least about 60, at least about 75, at least about 90, or at least about 100, and typically not more than about 2500, preferably not more than about 2000, for example not more than about 1750, not more than about 1500, not more than about 1250, or not more than about 1000. Alternatively, the Si:Al ratio of relatively high-silica aluminosilicates can be from about 150 to about 2000, for example from about 150 to about 1250.

Other non-limiting examples of aluminosilicate catalysts and compositions can be found, for instance, in U.S. Patent Application Publication No. 2003/0176751 and U.S. patent application Ser. Nos. 11/017,286 (filed Dec. 20, 2004) and 60/731,846 (filed Oct. 31, 2005), the disclosures of each of which are incorporated by reference herein.

Additional examples of molecular sieve particles used to make formulated molecular sieve catalyst according to this invention include zeolite as well as non-zeolite molecular sieves, and are of the large, medium, or small pore type. Non-limiting examples of these molecular sieves are the small pore molecular sieves, AEI, AFT, APC, ATN, ATT, ATV, AWW, BIK, CAS, CHA, CHI, DAC, DDR, EDI, ERI, GOO, KFI, LEV, LOV, LTA, MON, PAU, PHI, RHO, ROG, THO, and substituted forms thereof, the medium pore molecular sieves, AFO, AEL, EUO, HEU, FER, MEL, MFI, MTW, MTT, TON, and substituted forms thereof, and the large pore molecular sieves, EMT, FAU, and substituted forms thereof. Other molecular sieves include ANA, BEA, CFI, CLO, DON, GIS, LTL, MER, MOR, MWW, and SOD. Non-limiting examples of the preferred molecular sieves, particularly for converting an oxygenate containing feedstock into olefin(s), include AEL, AFY, BEA, CHA, EDI, FAU, FER, GIS, LTA, LTL, MER, MFI, MOR, MTT, MWW, TAM, and TON. In one preferred embodiment, the molecular sieve of the invention contains an AEI topology, a CHA topology, or a combination thereof, most preferably one of the latter two.

In one embodiment, the molecular sieve crystal is an intergrowth material having two or more distinct phases of crystalline structures within one molecular sieve composition. In another embodiment, the molecular sieve crystal comprises at least one intergrown phase of AEI and CHA framework-types. For example, SAPO-18, AlPO-18 and RUW-18 have an AEI framework-type, and SAPO-34 has a CHA framework-type. In a further embodiment, the molecular sieve crystal comprises a mixture of intergrown material and non-intergrown material.

Where the crystalline (catalyst) material of the invention comprises a mixture of CHA and AEI or an intergrowth of a CHA framework and an AEI framework, the material can possess a widely varying AEI/CHA ratio of from about 99:1 to about 1:99, such as from about 98:2 to about 2:98, for example from about 95:5 to about 5:95. In one embodiment, where the material is to be used a catalyst in the conversion of oxygenates to olefins, the intergrowth can preferably be CHA-rich and can advantageously have a AEI/CHA ratio ranging from about 3:97 to about 40:60, more preferably from about 5:95 to about 30:70. In addition, in some cases the intergrown material of the invention may comprise a plurality of intergrown phases with a distribution of different AEI/CHA ratios. The relative amounts of AEI and CHA framework-types in the intergrowth can be determined by a variety of known techniques, including, but not limited to, transmission electron microscopy (TEM) and DIFFaX analysis, using the powder X-ray diffraction pattern of a calcined sample of the catalyst.

Another type of olefin-forming catalyst capable of producing large quantities of ethylene and propylene is a silicoaluminophosphate (SAPO) molecular sieve. Silicoaluminophosphate molecular sieves are generally classified as being microporous materials having 8-, 10-, or 12-membered ring structures. These ring structures can have an average pore size ranging from about 3.5 to about 15 angstroms. Preferred are the small pore SAPO molecular sieves having an average pore size of less than or equal to about 5 angstroms, preferably an average pore size ranging from about 3.5 to about 5 angstroms, more preferably from about 3.5 to about 4.2 angstroms. These pore sizes are typical of molecular sieves having 8-membered rings.

According to one embodiment, substituted SAPOs can also be used in oxygenate-to-olefin reaction processes. These compounds are generally known as MeAPSOs or metal-containing silicoaluminophosphates. The metal can be alkali metal ions (Group IA), alkaline earth metal ions (Group IIA), rare earth ions (Group IIIB, including the lanthanide elements: lanthanum, cerium, praseodymium, neodymium, samarium, europium, gadolinium, terbium, dysprosium, holmium, erbium, thulium, ytterbium and lutetium; and scandium or yttrium), and the additional transition cations of Groups IVB, VB, VIIB, VIIB, VIIIB, and IB.

Preferably, the Me represents atoms such as Zn, Mg, Mn, Co, Ni, Ga, Fe, Ti, Zr, Ge, Sn, and Cr. These atoms can be inserted into the tetrahedral framework through a [MeO$_2$] tetrahedral unit. The [MeO$_2$] tetrahedral unit carries a net electric charge depending on the valence state of the metal substituent. When the metal component has a valence state of +2, +3, +4, +5, or +6, the net electric charge is between −2 and +2. Incorporation of the metal component is typically accomplished by adding the metal component during synthesis of the molecular sieve. However, post-synthesis ion exchange can also be used. In post synthesis exchange, the metal component will introduce cations into ion-exchange positions at an open surface of the molecular sieve, not into the framework itself.

Suitable silicoaluminophosphate molecular sieves include SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, the metal containing forms thereof, and mixtures thereof. Preferred are SAPO-18, SAPO-34, SAPO-35, SAPO-44, and SAPO-47, particularly SAPO-18 and SAPO-34, including the metal containing forms thereof, and mixtures thereof. As used herein, the term mixture is synonymous with combination and is considered a composition of matter having two or more components in varying proportions, regardless of their physical state.

An aluminophosphate (ALPO) molecular sieve can also be included in the catalyst composition. Aluminophosphate molecular sieves are crystalline microporous oxides, which can have an AlPO$_4$ framework. They can have additional elements within the framework, typically have uniform pore dimensions ranging from about 3 angstroms to about 10 angstroms, and are capable of making size-selective separations of molecular species. More than two dozen structure types have been reported, including zeolite topological analogues. Preferred ALPO structures are ALPO-5, ALPO-11, ALPO-18, ALPO-31, ALPO-34, ALPO-36, ALPO-37, and ALPO-46.

The ALPOs can also include metal substituents in their frameworks. Preferably, the metal is selected from the group consisting of magnesium, manganese, zinc, cobalt, and mixtures thereof. These materials preferably exhibit adsorption, ion-exchange and/or catalytic properties similar to aluminosilicate, aluminophosphate and silica aluminophosphate molecular sieve compositions.

The metal-containing ALPOs have a three-dimensional microporous crystal framework structure of MO$_2$, AlO$_2$ and PO$_2$ tetrahedral units. These as-manufactured structures (which contain template prior to calcination) can be represented by an empirical chemical composition, on an anhydrous basis, as mR:(M$_x$Al$_y$P$_z$)O$_2$, wherein: "R" represents at least one organic templating agent present, preferably an organic templating agent, in the intracrystalline pore system; "m" represents the moles of "R" present per mole of (M$_x$Al$_y$P$_z$)O$_2$ and has a value of from 0 to 1, preferably 0 to 0.5, and most preferably from 0 to 0.3, the maximum value in each case depending upon the molecular dimensions of the templating agent and the available void volume of the pore system of the particular metal aluminophosphate involved; "x," "y," and "z" represent the mole fractions of the metal "M," aluminum, and phosphorus, respectively, present as tetrahedral oxides; M is a metal selected from one of Group IA, IIA, IB, IIIB, IVB, VB, VIIB, VIIB, VIIIB, and Lanthanides of the Periodic Table of Elements, preferably selected from one of the group consisting of Si, Ge, Co, Cr, Cu, Fe, Ga, Ge, Mg, Mn, Ni, Sn, Ti, Zn, Zr, and mixtures thereof (e.g., magnesium, manganese, zinc, and cobalt). In a particular embodiment, m is greater than or equal to 0.2, and x, y and z are greater than or equal to 0.01. Additionally or alternately, in some embodiments, m can be from about 0.1 to about 1, x can be from about 0.01 to about 0.25, y can be from about 0.4 to about 0.5, and z can be from about 0.25 to about 0.5; more preferably m can be from about 0.15 to about 0.7, x can be from about 0.01 to about 0.2, y can be from about 0.4 to about 0.5, and z can be from about 0.3 to about 0.5. For the purposes of the present invention, a "templating agent" is any substance as a result of which the solid which is formed during generation of the at least one material from the synthesis mixture has at least one type of pore (micropores, mesopores, macropores).

The metal-containing ALPOs are sometimes referred to by the acronym MeAPO. Also in those cases where the metal "Me" in the composition is magnesium, the acronym MAPO is applied to the composition. Similarly ZAPO, MnAPO and CoAPO are applied to the compositions which contain zinc, manganese and cobalt respectively. To identify the various structural species which make up each of the subgeneric classes MAPO, ZAPO, CoAPO and MnAPO, each species is assigned a number and is identified, for example, as ZAPO-5, MAPO-11, CoAPO-34 and so forth.

Other examples of metalloaluminophosphate molecular sieves useful in the process of this invention include those described in EP-0 888 187 B1 (microporous crystalline metallophosphates, SAPO$_4$ (UIO-6)), U.S. Pat. No. 6,004,898 (molecular sieve and an alkaline earth metal), PCT WO 01/62382 published Aug. 30, 2001 (integrated hydrocarbon co-catalyst), PCT WO 01/64340 published Sep. 7, 2001 (thorium containing molecular sieve), and R. Szostak, *Handbook of Molecular Sieves*, Van Nostrand: Reinhold, New York, N.Y. (1992), which are all herein fully incorporated by reference.

When a metalloaluminophosphate is desired, the molecular sieve crystals present in the molecular sieve catalyst composition are most preferably selected from the group consisting of silicoaluminophosphate (SAPO) molecular sieves, aluminophosphate molecular sieves, and metal substituted forms thereof. Non-limiting examples of SAPO and AlPO molecular sieves that may be present in the molecular sieve catalyst of the invention include molecular sieves selected from the group consisting of SAPO-5, SAPO-8, SAPO-11, SAPO-16, SAPO-17, SAPO-18, SAPO-20, SAPO-31, SAPO-34, SAPO-35, SAPO-36, SAPO-37, SAPO-40, SAPO-41, SAPO-42, SAPO-44, SAPO-47, SAPO-56, AlPO-5, AlPO-11, AlPO-18, AlPO-31, AlPO-34, AlPO-36, AlPO-37, AlPO-46, metal containing molecular sieves thereof, and mixtures thereof. The more preferred molecular sieves include molecular sieves selected from the group consisting of SAPO-18, SAPO-34, SAPO-35, SAPO-44, SAPO-56, AlPO-18 AlPO-34, metal containing molecular sieves thereof, and mixtures thereof, even more preferably molecular sieves selected from the group consisting of SAPO-18, SAPO-34, AlPO-34, AlPO-18, metal containing molecular sieves thereof, and mixtures thereof, and most preferably molecular sieves selected from the group consisting of SAPO-34, AlPO-18, metal containing molecular sieves thereof, and mixtures thereof.

As used herein, the term mixture is synonymous with combination and is considered a composition of matter having two or more components in varying proportions, regardless of their physical state. With regard to the molecular sieve crystal components of the catalyst, the term further encompasses physical mixtures of crystalline and amorphous components, as well as intergrowths of at least two different molecular sieve structures, such as, for example, those described in PCT Publication No. WO 98/15496 and in U.S. Pat. No. 7,094,389.

Without being bound by theory, it is believed that molecular sieves having relatively small crystal sizes, and/or those having relatively large crystal sizes but having too many impurities (e.g., from over-flocculation during isolation and recovery of the molecular sieve during formulation), can be particularly susceptible to having relatively higher initial slurry, or "zero pass," viscosities, when pre-mixed with both the matrix material and the binder component. Therefore, it is believed that the most profound application for the controlled and ordered addition of catalyst composition components is for those molecular sieves that are particularly susceptible to relatively high zero pass viscosities in the absence of said controlled and ordered component addition. Indeed, in many cases, it is further believed that the useful lifetime of a catalyst composition can be particularly impacted by molecular sieve crystal size, by molecular sieve impurity level, by slurry viscosity upon formulation, or by a combination of these three factors.

Materials can be blended with the molecular sieve to form what is generally referred to as formulated catalyst. Such blended materials can be various inert or catalytically active materials, or various binder materials. These materials include compositions such as kaolin and other clays, various forms of rare earth metals, metal oxides, other non-zeolite catalyst components, zeolite catalyst components, alumina or alumina sol, titania, zirconia, magnesia, thoria, beryllia, quartz, silica or silica or silica sol, and mixtures thereof. These components are also effective in reducing, inter alia, overall catalyst cost, and acting as a thermal sink to assist in heat shielding the catalyst during regeneration, densifying the catalyst and increasing catalyst strength. It is particularly desirable that the inert materials that are used in the catalyst to act as a thermal sink have a heat capacity of from about 0.05 to about 1 cal/g·°C., more preferably from about 0.1 to about 0.8 cal/g·°C., most preferably from about 0.1 to about 0.5 cal/g·°C.

The catalyst composition, according to an embodiment, preferably comprises from about 1% to about 99%, more preferably from about 5% to about 90%, and most preferably from about 10% to about 80%, by weight of molecular sieve. It is also preferred that the catalyst composition have a particle size of from about 20 microns to about 3,000 microns, more preferably from about 22 microns to about 200 microns, most preferably from about 25 microns to about 150 microns.

A molecular sieve catalyst particularly useful in making ethylene and propylene is a catalyst that contains a combination of SAPO-34, SAPO-18, and/or ALPO-18 molecular sieve. In a particular embodiment, the molecular sieve is a crystalline intergrowth of SAPO-34 and either SAPO-18 or ALPO-18. To convert oxygenate to olefin, conventional reactor systems can be used, including fixed-bed, fluid-bed or moving-bed systems. Preferred reactors of one embodiment are co-current riser reactors and short contact time, counter-current free-fall reactors. Desirably, the reactor is one in which an oxygenate feedstock can be contacted with a molecular sieve catalyst at a weight hourly space velocity (WHSV) of at least about 1 $hr^{-1}$, preferably in the range of from about 1 $hr^{-1}$ to 1000 $hr^{-1}$, more preferably in the range of from about 20 $hr^{-1}$ to about 1000 $hr^{-1}$, and most preferably in the range of from about 25 $hr^{-1}$ to about 500 $hr^{-1}$. WHSV is defined herein as the weight of oxygenate, and reactive hydrocarbon which may optionally be in the feed, per hour per weight of the molecular sieve in the reactor. Because the catalyst or the feedstock may contain other materials which act as inerts or diluents, the WHSV is calculated on the weight basis of the oxygenate feed, and any reactive hydrocarbon which may be present with the oxygenate feed, and the molecular sieve contained in the reactor.

The process can generally be carried out at a wide range of temperatures. An effective operating temperature range can be from about 200° C. to about 700° C., preferably from about 300° C. to about 600° C., more preferably from about 350° C. to about 550° C. At the lower end of the temperature range, the formation of the desired olefin products may become markedly slow with a relatively high content of oxygenated olefin byproducts being found in the olefin product. However, the selectivity to ethylene and propylene at reduced temperatures may be increased. At the upper end of the temperature range, the process may not form an optimum amount of ethylene and propylene product, but the conversion of oxygenate feed will generally be high.

Operating pressure also may vary over a wide range, including autogenous pressures. Effective pressures include, but are not necessarily limited to, a total pressure of at least 1 psia (7 kPaa), preferably at least about 5 psia (34 kPaa). The process is particularly effective at higher total pressures, including a total pressure of at least about 20 psia (138 kPaa). Preferably, the total pressure is at least about 25 psia (172 kPaa), more preferably at least about 30 psia (207 kPaa). For practical design purposes it is desirable to use methanol as the primary oxygenate feed component and operate the reactor at a pressure of not greater than about 500 psia (3445 kPaa), preferably not greater than about 400 psia (2756 kPaa), most preferably not greater than about 300 psia (2067 kPaa).

Undesirable byproducts can be avoided by operating at an appropriate gas superficial velocity. As the gas superficial velocity increases, the conversion decreases, avoiding undesirable byproducts. As used herein, the term, "gas superficial velocity" is defined as the combined volumetric flow rate of vaporized feedstock, which includes diluent when present in the feedstock, as well as conversion products, divided by the cross-sectional area of the reaction zone. Because the oxygenate is converted to a product having significant quantities of ethylene and propylene while flowing through the reaction zone, the gas superficial velocity may vary at different locations within the reaction zone. The degree of variation depends on the total number of moles of gas present and the cross section of a particular location in the reaction zone, temperature, pressure and other relevant reaction parameters.

In one embodiment, the gas superficial velocity is maintained at a rate of greater than 1 meter per second (m/s) at one or more points in the reaction zone. In another embodiment, it is desirable that the gas superficial velocity is greater than about 2 m/s at one or more points in the reaction zone. More desirably, the gas superficial velocity is greater than about 2.5 m/s at one or more points in the reaction zone. Even more desirably, the gas superficial velocity is greater than about 4 m/s at one or more points in the reaction zone. Most desirably, the gas superficial velocity is greater than about 8 m/s at one or more points in the reaction zone.

III. Removing Water and Solid from the Olefin Product

The oxygenate-to-olefin process forms a substantial amount of water as a byproduct. Much of this water byproduct can be removed from the olefin product of the oxygenate-toolefin process by cooling the olefin product and condensing at least a portion of the product to form an olefin vapor stream and a condensed, liquid stream, with the condensed stream containing a substantial amount of water. This condensed stream will also typically contain solid materials, such as inorganic oxide particles, entrained in the olefin product. In particular, the majority of the solids materials are catalyst particles that become entrained with the olefin product as the product leaves the oxygenate-to-olefins reaction process.

The solid material that condenses out of the olefin product stream with the condensed water can deposit on the condensing equipment causing significant fouling of the equipment surfaces that are in contact with the condensed liquid stream. This effect is particularly significant for cooling equipment, such as heat exchangers, where the fouling causes a loss in heat transfer efficiency. This invention provides a way to reduce or eliminate fouling in the condensing or quench system. This reduction or elimination is achieved by injecting an antifouling agent into a water condensing or quench system in an amount to maintain (i) a zeta potential of fouling liquid (i.e., the zeta potential of the entrained solids and/or catalyst particles contained in the condensed liquid) and (ii) an effective zeta potential of the surface of the quench system in contact with the condensed liquid, where both zeta potentials are in a positive range or both are in a negative range. The "effective zeta potential" of the equipment surface is the zeta potential that the surface's constituents would have if they were suspended as small particles in water and measured in accordance with conventional zeta potential measurement techniques. It has been discovered that fouling can be reduced by regulating the pH of the condensed liquid stream so that the zeta potential of the foulants in the condensed liquid and the effective zeta potential of the equipment surface are simultaneously either both positive or both negative. Consequently, in one embodiment the antifouling agent is a material added to the condensed liquid stream which is capable of regulating the pH of the condensed liquid stream.

It has also been discovered that the relationship between the zeta potential of the foulant in the condensed liquid stream and the effective zeta potential of the equipment surface can be controlled to be either both negative or both positive without changing pH. Consequently, in another embodiment the antifouling agent is a material, such as a cationic polymer, that can alter the isoelectric point ("IEP") of the condensed liquid stream without changing or substantially changing pH.

Surface charge or zeta potential of a particle can be altered by a number of means. The most commonly practiced means of altering zeta potential include the addition of water-soluble ionic materials. The presence or adsorption of the water-soluble ionic materials leads to major changes in surface charge. However, introduction of metal cations or anions into the quench system of an OTO process can lead to poisoning or alteration of the oxygenate-to-olefins catalyst; thus, they are less preferred than organic ionic compounds. There are three types of water-soluble organic ionic materials: (1) cationic; (2) anionic; and (3) zwitterionic. Zwitterionic materials contain both an anionic and a cationic charge under normal conditions, e.g., molecules containing a quaternary ammonium group as the cationic group and a carboxylic group as the anionic group.

Anionics

Carboxylate, sulfate, sulfonate and phosphate are the typical polar groups found in anionic polymers. Examples of water-soluble anionic polymers are: dextran sulfates, high molecular weight ligninsulfonates prepared by a condensation reaction of formaldehyde with ligninsulfonates, and polyacrylamide. Commercially available anionic water soluble polymers include polyacrylamide, CYANAMER series from Cytec Industries Inc., West Paterson, N.J., such as, A-370M/2370, P-35/P-70, P-80, P-94, F-100L & A-15; CYANAFLOC 310L, CYANAFLOC 165S.

Cationics

Many cationic polymers are based on the nitrogen atom carrying the cationic charge. Both amine and quaternary ammonium-based products are common. The amines only function as an effective surface modifier in the protonated state; therefore, they cannot be used at high pH. Quaternary ammonium compounds, however, are not pH sensitive. Ethoxylated amines possess properties characteristic of both cationic and non-ionic materials, depending on chain length. Examples of water-soluble cationic polymers are: polyethyleneimine, polyacrylamide-co-trimethylammonium ethyl methyl acrylate chloride (PTAMC), and poly(N-methyl-4-vinylpyridinium iodide). Commercially available materials include: Cat Floc 8108 Plus, 8102 Plus, 8103 Plus, from Nalco Chemicals, Sugar Land, Tex.; polyamines, Superfloc C500 series from Cytec Industries Inc., West Paterson, N.J., including C-521, C-567, C-572, C-573, C-577, and C-578 of different molecular weights; poly diallyl, dimethyl, ammonium chloride (poly DADMAC) C-500 series, C-587, C-591, C-592, and C-595 of varying molecular weights and charge density, and low molecular weight and high charge density C-501.

Zwitterionics

Common types of zwitterionic compounds include N-alkyl derivatives of simple amino acids, such as glycine ($NH_2CH_2COOH$), amino propionic acid ($NH_2CH_2CH_2COOH$) or polymers containing such structure segments or functional groups.

As is known, the isoelectric point of an aqueous system of dispersed particles is the pH at which the particles show no electrophoretic mobility and where the zeta potential has a value of zero. Preferably, the antifouling agent is injected into the quench system in an amount to maintain a zeta potential of the condensed water and entrained catalyst fraction and a zeta potential of a metal surface of the quench system in contact with the condensed water both in a positive range or both in a negative range.

In another embodiment, the IEP of the foulant in the condensed liquid stream and the IEP of the constituent metal oxides of the equipment surface are determined. Although the equipment surface is described herein as having "constituent metal oxides," this is only for convenience. Indeed, the metal of the equipment surface may be oxidized and/or reduced by reacting with atoms other than oxygen to form non-metallic surfaces. Such non-metallic surfaces can include, but are not limited to, metal nitrides, metal nitrites, metal nitrates, metal oxynitrides, metal sulfides, metal hydrosulfides, metal sulfites, metal hydrosulfites, metal sulfates, metal hydrosulfates, metal sulfonates, metal oxysulfides, metal phosphides, metal phosphites, metal phosphates, metal hypophosphites, metal oxycarbides, metal carboxides, metal hydroxides, and the like, and a combination thereof. Even though surfaces may be described herein as comprising metal oxides, it should be understood that they can additionally or alternately comprise other non-metallic surface components, such as those listed in this paragraph.

Figure 6:
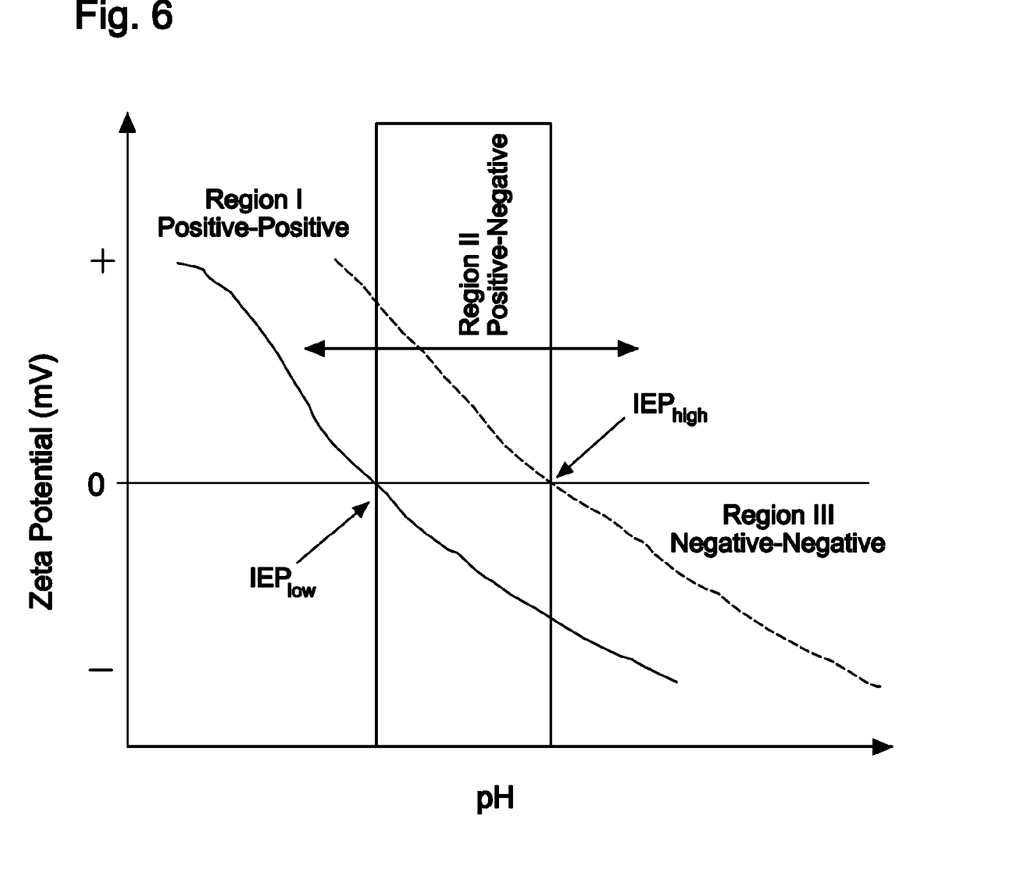
FIG. 6 demonstrates embodiments wherein the IEPs have been determined where the solid line represents the zeta potential of the material with the lower IEP and the dashed line represents the zeta potential of the material with the higher IEP; the shaded region between the higher and lower IEPs is not a preferred region of pH.

Any technique capable of determining IEP can be used, including conventional techniques such as zeta potential measurement and electrophoresis. For example, conventional techniques can be used to observe the mobility of dispersed particles in the presence of an applied electric field in an electrophoretic cell. Acid or base can be added to the cell while observing the dispersed particles' electrophoretic mobility. The value of the dispersed particles' IEP is equal to the pH at which the particles' electrophoretic mobility is zero (within experimental error). Once the IEPs have been determined, either (i) an acid is added to the condensed liquid stream to decrease the pH of the condensed liquid stream to a value below the lesser of the two the measured IEPs or (ii) a base is added to the condensed liquid stream to increase the pH of the condensed liquid stream to a value above the greater of the two measured IEPs. This embodiment is illustrated in FIG. 6, where the solid line represents the zeta potential of the material with the lower IEP (usually but not always the foulant in the condensed liquid stream) and the dashed line represents the zeta potential of the material with the higher IEP (usually but not always the constituent metal or metal oxide of the heat transfer surface). The shaded region between the higher and lower IEPs is not a preferred region of pH. While not wishing to be bound by any theory or model, it is believed that in the shaded region, where one zeta potential is positive and the other negative, an electrical attraction will subsist between the foulant and the equipment surface, leading to the undesirable deposition of foulant on or near the equipment surface. In cases where the equipment surface comprises two or more metals and/or metal oxides with different IEPs, the IEP of metal oxide with the highest IEP value among them is preferably used to determine the upper pH boundary of the shaded region. If more than one foulant is present, the IEP of the foulant with the lowest IEP among them is used to determine the lower pH boundary of the shaded region. Naturally, this situation is reversed when the foulants have a higher IEP than the metals/metal oxides, i.e., when the zeta potential of the metals and metal oxides are represented by the solid line in FIG. 6 and the foulant zeta potential represented by the dashed line. The preferred region is at a pH below the $IEP_{low}$, where all surfaces are positively charged, or above the $IEP_{high}$, where all surfaces are negatively charged.

In an embodiment, the foulant IEP is in the range of from about 5.6 to about 5.9, and the metal oxide IEP is in the range of from about 7.5 to about 8.5.

Preferably, the olefin product from the oxygenate-to-olefin process is cooled to a temperature below the condensation temperature of the water vapor in the stream in order to condense the undesirable byproducts. More particularly, the temperature of the olefin product stream is cooled to a temperature below the condensation temperature of the oxygenate feed used in the oxygenate-to-olefin process. In certain embodiments, the olefin product is cooled below the condensation temperature of ethanol. Upon condensation, a liquid stream is formed that is rich in water byproduct. The vapor stream that remains following condensation is rich in olefins, particularly light olefins (e.g., one or more of ethylene, propylene and butylene).

In one embodiment, the olefin product stream is cooled in a quench system to form an olefin fraction and a condensed water and entrained catalyst fraction (i.e., the condensed liquid stream comprises the condensed water and entrained catalyst), wherein the quench system is comprised of a surface structure. The surface structure can be any of a variety of materials suitable for heat transfer. Examples include carbon steels; stainless steels such as 302, 304/304L, 304, 304H, 309S, 310S, 316/316L, 317/317L, 347, 254 SMO® (available from Letco Ind., Springfield, Mo.); nickel alloys including 200/201, 400, 600, 625, C-276, C-22®, C-2000®, B-3®, G-30®, AL-6XN®, (all available from Letco Ind., Springfield, Mo.), 20, 800, 825, 904L; Hastelloy™; titanium and titanium alloys including Pb-stabilized titanium; and tantalum and tantalum alloys; duplex stainless steels including 2205, 2304, 2507; fluoropolymers (available, for instance, from AMETEK Chemical Products, Wilmington, Del.); poly-silica-coated metals [e.g., produced by deposition and curing of hexamethyldisiloxane (HMDSO) or octyltriethoxysilane (OTES)].

Figure 5:
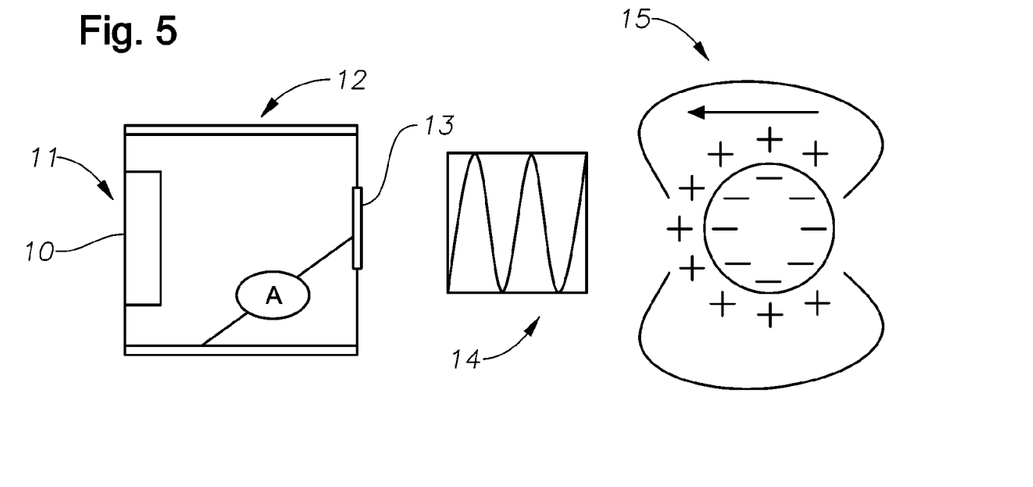
FIG. 5 illustrates schematically the zeta potential of dispersed particles in a fluid can be conveniently measured by conventional acoustic and electroacoustic techniques.

The zeta potential of dispersed particles in a fluid can be conveniently measured by conventional acoustic and electroacoustic techniques, as illustrated schematically in FIG. 5. Referring to the figure, a piezoelectric crystal 11 is used to measure the pressure gradient created by the ultrasound. A surface current produced due to the interaction between the ultrasound field and the electrical double layer of the particle surface is measured by electrodes 12 and 13. Using the relationship $$CVC = \left[\frac{(\rho_p - \rho_s)}{\rho_s}\right]\Phi\mu_d \nabla P$$

the dynamic mobility, $\mu_d$, of the particles can be determined using the relationship $$\mu_d = \left[\frac{\varepsilon_m \varepsilon_0 \zeta}{\eta}\right]\left[\frac{(\rho_p - \rho_s)\rho_m K_s}{(\rho_p - \rho_m)\rho_s K_m}\right]$$

The zeta potential, $\zeta$, can then be calculated directly from the dynamic mobility. In these equations, CVC is the colloidal vibration current, $\rho_p$ is the density of the particle; $\rho_m$ is the density of the fluid medium; $\Phi$ is the weight fraction of particles; $\nabla P$ is the pressure gradient in the cell; $\varepsilon_m$ is the electrical permittivity of the fluid medium; $\varepsilon_0$ is the electrical permittivity of a vacuum; $\eta$ is the dynamic viscosity of the medium; $\rho_s$ is the density of the suspension; $K_s$ is the conductivity of the suspension; and $K_m$ is the conductivity of the fluid medium. Details on the theory of measurement are available in Dukhin, A. S, and P. J. Goetz, *Ultrasound for Characterizing Colloids Particle Sizing, Zeta Potential, Rheology*, Amsterdam: Elsevier Press, 2002 (pp. 153-169).

For water suspension samples, the inputs required for measuring zeta potential are the weight fraction of the sample in the suspension and the density of the sample, since the density, the electrical permittivity, and the viscosity of water are known and already stored in the DT 1200 instrument database and since particle size is measured by the instrument. Alternatively, the measurement can be made using predetermined particle-size information, a so-called a priori measurement that skips the particle-size measurement function of the instrument.

The zeta potential of the foulant in the condensed liquid stream can be conveniently measured by sampling the foulant from the oxygenate-to-olefin reactor system and then measuring the zeta potential in the electroacoustic cell using the method described above. If necessary the foulant can be recovered for measurement by using a filter. One type of filter that can be used is made of polypropylene fibers (5 microns in diameter). The filter has the ability to collect particles greater than 0.5 microns. The recovered sample is then dispersed in de-ionized water to give a suspension of 1.5 to 10 wt % foulant for zeta potential measurement. Depending on the state or size of the foulant sample, mixing may be applied to improve dispersion. One type of mixing that can be used is high-shear mixing, e.g., using a Silverson high shear mixer from Silverson Machines Inc., East Longmeadow, Mass., at 3000-4000 RPM for 1 to 10 minutes. The electroacoustic cell can then be used to measure effective zeta potential as described above.

In a preferred embodiment, the recovered sample is dispersed in a fractional sample of the filtrate rather than deionized water to ensure that any soluble ionic species recovered in the quench tower condensate are included in the dispersion. The mass of the fractional sample is such that the concentration of the resulting suspension is 1.5 to 10 wt % foulant.

An effective zeta potential of an extensive surface (such as that of a heat exchange device) can be measured in a similar fashion using powders produced from materials similar to those found in the extensive surface (e.g., powders of $Fe_2O_3$ or $Fe_3O_4$) or powder produced through grinding of a sample of the extensive surface itself.

Preferably, the zeta potential of the entrained catalyst fraction in the condensed water (together comprising the condensed liquid stream) and the effective zeta potential of the surface of the quench system in the condensed water both have an absolute value of at least 2 mV. More preferably, the zeta potential of the condensed water and entrained catalyst fraction and the effective zeta potential of the surface of the quench system in the condensed water both have an absolute value of at least 3 mV, and most preferably at least 4 mV.

In one embodiment, (i) the zeta potential of the entrained catalyst fraction in the condensed water and (ii) the effective zeta potential of the surface of the quench system in the condensed water both have a value of at least +2 mV. More preferably, the zeta potential of the entrained catalyst in the condensed water and the effective zeta potential of the surface of the quench system in the condensed water both have a value of at least +3 mV, and most preferably at least +4 mV.

In another embodiment, the zeta potential of the entrained catalyst in the condensed water and the effective zeta potential of the surface of the quench system in the condensed water both have a value of −2 mV or less. More preferably, the zeta potential of the entrained catalyst in the condensed water and the effective zeta potential of the surface of the quench system in the condensed water both have a value of −3 mV or less, and most preferably −4 mV or less.

It is not necessary that the zeta potential of both the entrained catalyst in the condensed water and the effective zeta potential of the surface of the quench system in the condensed water have very large absolute values to be effective. In one embodiment, at least one of (i) the entrained catalyst in the condensed water and (ii) the surface of the quench system in the condensed water has a zeta potential or effective zeta potential that has an absolute value of not greater than 25 mV. In one embodiment, at least one of (i) the zeta potential of the entrained catalyst in the condensed water and (ii) the effective zeta potential of the surface of the quench system in the condensed water has an absolute value of not greater than 20 mV.

In one embodiment, the surface structure of the fouled surface (or the surface being fouled) can be increasingly (as time goes on) substantially identical in chemical composition to the molecular sieve catalyst in the entrained solids flowing through the separation system. In other words, in some embodiments, the molecular sieve fines that are contained in the entrained solids can deposit on, react with, and/or in some fashion oxidize the equipment surface(s) to form a partial (or complete, in the case of severe fouling) coating thereon. In such an embodiment, therefore, the IEP of the molecular sieve and the IEP of the fouled/fouling surface can become increasingly substantially similar. In such a case, it can be particularly desirable to use an antifouling agent according to the process of the invention to prevent, inhibit, and/or reduce the severity of such fouling of the equipment surfaces.

The antifouling agent that is injected is preferably a catalyst-surface affecting agent or an agent that affects the surface of the quench system. Preferably, the agent includes an acid, a base, or a surface modifier. In other words, the antifouling agent can be a material that affects a solution's pH (such as an acid or a base), a material that affects a solution's zeta potential without significantly affecting the solution's pH (such as an ionic polymer), and combinations thereof.

In one embodiment, the agent is an acid or base. Preferably, the acid or base is injected into the quench system in an amount to maintain a pH in the quench system of less than 6 or greater than 8. Preferably, the acid or base is injected into the quench system to maintain a pH in the quench system of from 4 to 6. Still more preferably, an acid or base is injected into the quench system to maintain a pH in the quench system of from 5 to 6, and most preferably from 5 to 5.5. In a particular embodiment, a base is injected to maintain a pH in the quench system of less than 6 or in the range of from 4 to 6, preferably 5 to 6, and more preferably from 5 to 5.5. In one related embodiment, (i) the condensed liquid stream comprises water and foulant, (ii) the foulant comprises oxygenate-to-olefin catalyst fines, and (iii) the equipment surface is the tube side or jacket side of a heat exchanger having a ferritic surface in contact with the foulant where the analogous metal oxides (for the purpose of measuring effective zeta potential) are $Fe_2O_3$ and $Fe_3O_4$.

Following condensation, at least a portion of the condensed water and entrained catalyst fraction is separated from the olefin fraction. The quench system includes any vessel or equipment that is involved in separating the condensed water and entrained catalyst fraction from the olefin fraction. Preferably, the quench system comprises at least one quench vessel and a pumparound system in fluid connection with the quench vessel.

In one embodiment, the pumparound system comprises at least one pump and at least one cooling vessel. The cooling vessel is preferably a heat exchange system or heat exchanger that is used to cool at least a portion of the condensed water. The cooled condensed water is preferably recycled back to the quench vessel to aid in condensation.

The quench vessel also optionally includes a settling system for removal of either solids or a second liquid phase or both. The settling system can be within the quench vessel itself or it can be a separate vessel. Preferably, the settling system is located prior to the pumparound to act in addition as a surge vessel. Additional vapor can also be removed from the settling system, and a water fraction from the settling system is recycled through the pumparound system back to the quench vessel. The antifouling agent can be added to the settling system or before or after the settling system if desired.

A settling system can also be included in the pumparound system. Preferably, in this embodiment the settling system follows the pump portion of the pumparound system. In this location, vapor can also be removed from the settling system and a water fraction from the settling system recycled to the quench vessel or sent on to further treatment such as for additional removal of byproducts or sent to wastewater treatment. The antifouling agent can be added to the settling system or before or after the settling system if desired.

The antifouling agent is injected into any portion of the quench system that enables the circulating water fraction to be maintained as desired. Preferably, the antifouling agent is injected into the quench vessel, the pumparound system or both. It is also preferred that at a point downstream of the injection point, the circulating water fraction be monitored for proper maintenance. For example, the circulating water system can be monitored downstream of the injection point for pH and the amount of the antifouling agent can be adjusted as appropriate to maintain the desired pH in the system.

In one embodiment, the olefin stream that is provided and sent to the quench system comprises ethylene and propylene, $C_{4+}$ olefins, methane, $C_{2+}$ paraffins, water, unreacted oxygenates, and oxygenated hydrocarbons. In another embodiment, the olefin stream comprises from about 30 wt % to about 70 wt % water, preferably, from about 35 wt % to about 70 wt % water; more preferably from about 40 wt % to about 65 wt % water expressed as a percentage of the total weight of the olefin stream.

In another embodiment, the olefin stream has about 2 wt % or less, preferably about 1 wt % or less, more preferably from about 0.005 wt % to about 0.5 wt % catalyst particles based upon the total weight of the olefin stream.

Typically, the olefin stream contains 40 wt % or more water, from about 50 wppm to about 2000 wppm carbon dioxide and from about 40 wt % to about 60 wt % olefins based upon the composition of the reactor effluent stream. There is an embodiment according to any process disclosed herein wherein the olefin stream further comprises from about 0.05 wt % to about 5 wt %, preferably from about 0.1 wt % to about 3 wt %, more preferably from about 0.2 wt % to about 3 wt %, even more preferably from about 1 wt % to about 2 wt %, most preferably of about 1.5 wt % alcohol, particularly methanol, based upon the total weight of the olefin stream.

The quench system in one embodiment can include single or multiple heat transfer stages (e.g., heat exchangers), preferably two to four stages, more preferably two to three stages. The quench vessel can be embodied as a single vessel or as multiple vessels, including vessels such as flash drums or distillation-type columns.

In one embodiment, the quench vessel includes internal elements. Examples of internal elements include liquid distributors and contacting devices such as baffles, trays, random packing or structured packing. According to one embodiment, corrosion is inhibited in the quench system in at least portions of the system with a lining material capable of mitigating corrosion. In one embodiment, the lining material is a material selected from the group comprising glass, fluoropolymer (e.g., Teflon®), titanium and platinum.

Organic acids, i.e., acids that contain one or more carbon atoms that have at least one C—H bond can be added to the quench system to maintain pH in the desired range. Examples of such acids include formic acid, acetic acid, propanoic acid, and butyric acid, which includes their derivatives and salt forms.

Examples of bases include, for example, NaOH, KOH, $Ca(OH)_2$, CaO, $NH_4OH$, organic amines including basic quaternary ammonium compounds, and mixtures thereof.

The quench vessel is preferably maintained at a temperature that will enable the desired separation of olefin from condensable components. In one embodiment, the quench vessel is maintained at a bottoms temperature of from about 180° F. (82° C.) to about 300° F. (149° C.); preferably from about 180° F. (82° C.) to about 250° F. (121° C.). The temperature of the quench medium (i.e., quench recycle medium input into the quench vessel) is preferably from about 60° F. (15° C.) to about 200° F. (93° C.); more preferably from about 80° F. (27° C.) to about 140° F. (60° C.). The quench system is preferably operated at a pressure that is from about 15 psig (103 kPag) to about 50 psig (345 kPag); more preferably from about 15 psig (103 kPag) to about 40 psig (276 kPag).

In one embodiment, catalyst particles are included in the provided olefin stream, and a majority of the catalyst particles that are included in the olefin product stream are condensed out of the olefin stream along with the liquid fraction formed in the quench system. The term "majority" means more than 50%. According to one embodiment, the weight of the catalyst particles in the liquid fraction is about 5 wt % or less, preferably about 2 wt % or less, more preferably about 0.1 wt % or less based on the total weight of the liquid fraction. According to one embodiment, the weight of catalyst particles in the liquid fraction is about 10 wppm or greater based upon the total weight of the liquid fraction.

A vapor stream is removed or recovered from the quench system and this quenched vapor or effluent stream typically comprises light olefins including ethylene, propylene and butylene, dimethyl ether, methane, carbon monoxide, ethane, propane, and any water and unreacted oxygenate(s) such as alcohol (including methanol) that are not condensed during the operation of the quench system.

IV. Product Recovery

The olefin vapor stream that is separated out of or recovered from the quench system is preferably further processed to isolate and purify the various olefin components, particularly, ethylene and propylene. Any variety of recovery systems, techniques and sequences can be used to separate the desired olefin components that are recovered from the quench system. Such recovery systems generally comprise one or more or a combination of various separation, fractionation and/or distillation towers, columns, splitters, or trains, reaction systems and other associated equipment, for example, various condensers, heat exchangers, refrigeration systems or chill trains, compressors, knock-out drums or pots, pumps, and the like. Non-limiting examples of equipment used in a recovery system include one or more of a demethanizer, preferably a high-temperature demethanizer, a deethanizer, a depropanizer, membranes, ethylene ($C_2$) splitter, propylene ($C_3$) splitter, butene ($C_4$) splitter, and the like.

Generally accompanying most recovery systems is the production, generation or accumulation of additional products, byproducts and/or contaminants along with the preferred products. Examples of preferred products include light olefins, such as ethylene, propylene and/or butylene. Such products are typically purified for use in derivative manufacturing processes such as polymerization processes. In a preferred embodiment of the recovery system, the recovery system also includes a purification system. For example, light olefins produced particularly in an oxygenate-to-olefin process are passed through a purification system that removes low levels of byproducts or contaminants. Non-limiting examples of contaminants and byproducts include generally polar compounds such as water, alcohols, aldehydes, ketones, carboxylic acids, ethers, carbon oxides, ammonia and other nitrogen compounds, arsine, phosphine and chlorides. Other contaminants or byproducts include hydrogen and hydrocarbons such as acetylene, methyl acetylene, propadiene, butadiene and butyne.

Typically, in converting one or more oxygenates to olefins having 2 or 3 carbon atoms, an amount of hydrocarbons, particularly olefins, especially olefins having 4 or more carbon atoms, and other byproducts are formed or produced. Included in the recovery systems of the invention are reaction systems for converting the products contained within the olefin product stream withdrawn from the reactor or converting those products produced as a result of the recovery system utilized.

In one embodiment, the olefin product stream is passed through a recovery system producing one or more hydrocarbon containing streams, in particular, a three or more carbon atom ($C_{3+}$) hydrocarbon containing stream. In this embodiment, the $C_{3+}$ hydrocarbon containing stream is passed through a first fractionation zone producing a crude $C_3$ hydrocarbon and a $C_{4+}$ hydrocarbon containing stream, the $C_{4+}$ hydrocarbon containing stream is passed through a second fractionation zone producing a crude $C_4$ hydrocarbon and a $C_{5+}$ hydrocarbon containing stream. The four-or-more-carbon hydrocarbons include butenes such as butene-1 and butene-2, butadienes, saturated butanes, and isobutanes.

The olefin product stream removed from a conversion process, particularly an oxygenate-to-olefin process, typically contains hydrocarbons having 4 or more carbon atoms. The amount of hydrocarbons having 4 or more carbon atoms is typically in an amount less than 30 weight percent, preferably less than 25 weight percent, and most preferably less than 20 weight percent, based on the total weight of the olefin product stream withdrawn from an oxygenate-to-olefin process, excluding water. In particular with a conversion process of oxygenates into olefins utilizing a molecular sieve catalyst composition the resulting olefin product stream typically comprises a majority of ethylene and/or propylene and a lesser amount of four-carbon and higher carbon number products and other byproducts, excluding water.

The preferred light olefins produced by any one of the processes described above, preferably conversion processes, are high-purity prime olefin products that contain a $C_x$ olefin, wherein x is a number from 2 to 4, in an amount greater than 80 wt %, preferably greater than 90 wt %, more preferably greater than 95 wt %, and most preferably no less than about 99 wt %, based on the total weight of the olefin.

V. Olefin Product Use

Olefins recovered from the recovery system can be used in any variety of ways. For example, the $C_4$ hydrocarbons, butene-1 and butene-2 are used to make alcohols having 8 to 13 carbon atoms, and other specialty chemicals and isobutylene is used to make a gasoline additive, methyl-t-butylether, and isobutylene elastomers.

In another embodiment, recovered olefins are directed to one or more polymerization processes for producing various polyolefins. Polymerization processes include solution, gas phase, slurry phase and high pressure, or a combination thereof. Particularly preferred is a gas-phase or a slurry-phase polymerization of one or more olefins at least one of which is ethylene or propylene.

Examples of polymerization catalysts include Ziegler-Natta, Phillips-type, metallocene, metallocene-type polymerization catalysts, and mixtures thereof.

In one embodiment, the present invention comprises a polymerizing process of one or more olefins in the presence of a polymerization catalyst system in a polymerization reactor to produce one or more polymer products, wherein the one or more olefins have been made by converting an alcohol, particularly methanol, using a zeolite or zeolite-type molecular sieve catalyst composition. A preferred polymerization process is a gas-phase polymerization process and at least one of the olefins is either ethylene or propylene, and preferably the polymerization catalyst system is a supported metallocene catalyst system. In this embodiment, the supported metallocene catalyst system comprises a support, a metallocene or metallocene-type compound and an activator, preferably the activator is a non-coordinating anion or alumoxane, or combination thereof, and most preferably the activator is alumoxane.

Polymerization conditions vary depending on the polymerization process, polymerization catalyst system and the polyolefin produced. Typical conditions of polymerization pressure vary from about 100 psig (690 kPag) to greater than about 1000 psig (3448 kPag), preferably in the range of from about 200 psig (1379 kPag) to about 500 psig (3448 kPag), and more preferably in the range of from about 250 psig (1724 kPag) to about 350 psig (2414 kPag). Typical conditions of polymerization temperature vary from about 0° C. to about 500° C., preferably from about 30° C. to about 350° C., more preferably in the range of from about 60° C. to 250° C., and most preferably in the range of from about 70° C. to about 150° C. In the preferred polymerization process the amount of polymer being produced per hour is greater than 25,000 lbs/hr (11,300 kg/hr), preferably greater than 35,000 lbs/hr (15,900 kg/hr), more preferably greater than 50,000 lbs/hr (22,700 kg/hr) and most preferably greater than 75,000 lbs/hr (29,000 kg/hr).

The polymers produced by the polymerization processes described above include linear low-density polyethylene, elastomers, plastomers, high-density polyethylene, low-density polyethylene, polypropylene and polypropylene copolymers. The propylene-based polymers produced by the polymerization processes include atactic polypropylene, isotactic polypropylene, syndiotactic polypropylene, and propylene random, block or impact copolymers.

Typical ethylene-based polymers have a density in the range of from 0.86 g/cc to 0.97 g/cc, a weight-average molecular weight to number-average molecular weight ratio ($M_w/M_n$) of greater than 1.5 to about 10 as measured by gel permeation chromatography, a melt index ($I_2$) as measured by ASTM D-1238-E in the range from 0.01 dg/min to 1000 dg/min, a melt index ratio ($I_{21}/I_2$) ($I_{21}$ is measured by ASTM-D-1238-F) of from 10 to less than 25, alternatively a $I_{21}/I_2$ of from greater than 25, more preferably greater than 40.

Polymers produced by the polymerization process are useful in such forming operations as film, sheet, and fiber extrusion and co-extrusion as well as blow molding, injection molding and rotary molding; films include blown or cast films formed by coextrusion or by lamination useful as shrink film, cling film, stretch film, sealing films, oriented films, snack packaging, heavy duty bags, grocery sacks, baked and frozen food packaging, medical packaging, industrial liners, membranes, etc. in food-contact and non-food-contact applications; fibers include melt spinning, solution spinning and melt blown fiber operations for use in woven or non-woven form to make filters, diaper fabrics, medical garments, geotextiles, etc; extruded articles include medical tubing, wire and cable coatings, geomembranes, and pond liners; and molded articles include single and multi-layered constructions in the form of bottles, vessels, large hollow articles, rigid food containers and toys, etc.

In addition to polyolefins, numerous other olefin-derived products are formed from the olefins recovered in any one of the processes described above, particularly the conversion processes, more particularly the GTO process or MTO process. These include, but are not limited to, aldehydes, alcohols, acetic acid, linear alpha olefin(s), vinyl acetate, ethylene dichloride and vinyl chloride, ethylbenzene, ethylene oxide, cumene, isopropyl alcohol, acrolein, allyl chloride, propylene oxide, acrylic acid, ethylene-propylene elastomers, acrylonitrile, and dimers, trimers, and tetramers of ethylene, propylene or butylenes or mixtures thereof.

VI. Examples

Example 1

A sample of foulant obtained from a heat exchanger in a quench system of an oxygenates-to-olefins process was diluted in de-ionized water to make a slurry containing 5 wt % of the foulant. Samples of $Fe_2O_3$ (99.8% from Aldrich, Milwaukee, Wis.) and $Fe_3O_4$ (99.9% from Aldrich, Milwaukee, Wis.) were each dispersed in water to make a 5 wt % aqueous slurry of each oxide. The slurry was mixed using a Silverson (Silverson Machines Inc., East Longmeadow, Mass.) high-shear mixer at 3000-4000 RPM for 5 minutes. These oxides were selected as representative of the oxides present on the surface of steel and stainless steel heat exchange equipment, though it was recognized that other metals and metal oxides might be present on the heat exchanger surface in lesser amounts.

Zeta potential was measured as a function of pH using a DT 1200 Acoustic and Electroacoustic Spectrometer from Dispersion Technology Inc., Bedford Hills, N.Y. The foulant slurry had a starting pH of 8.26, the $Fe_2O_3$ slurry had a starting pH of 9.8, and the $Fe_3O_4$ slurry had a starting pH of 9.6. Acid was added to each slurry to generate the zeta potential curves and the IEPs. The results are given in FIGS. 1A, 1B, and 1C.

Figure 1A:
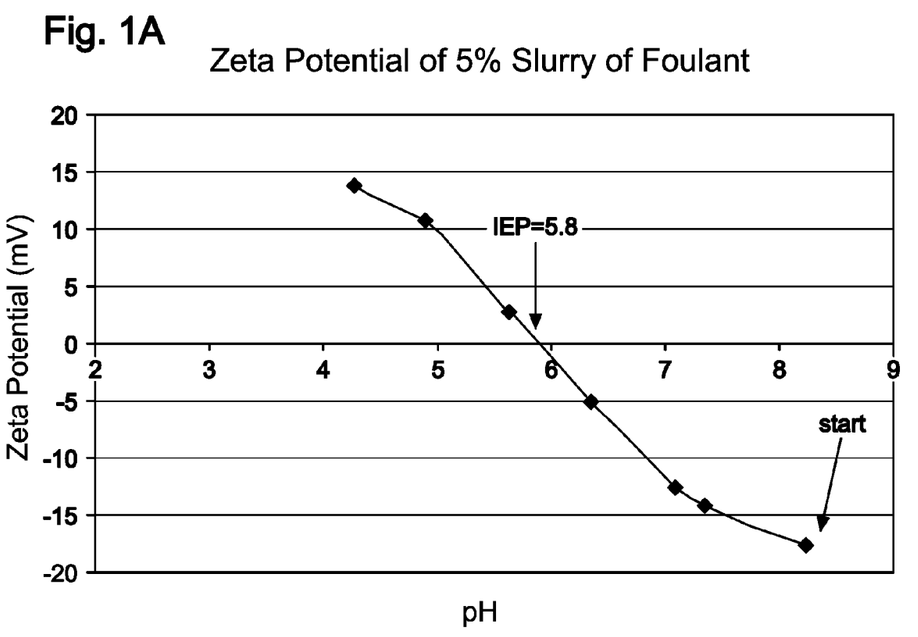
FIG. 1A relates to Example 1 and shows that the foulant has an isoelectric point (IEP) of 5.8; that is, the foulant is negatively charged at pH higher than 5.8 and positively charged at pH below 5.8.
Figure 1B:
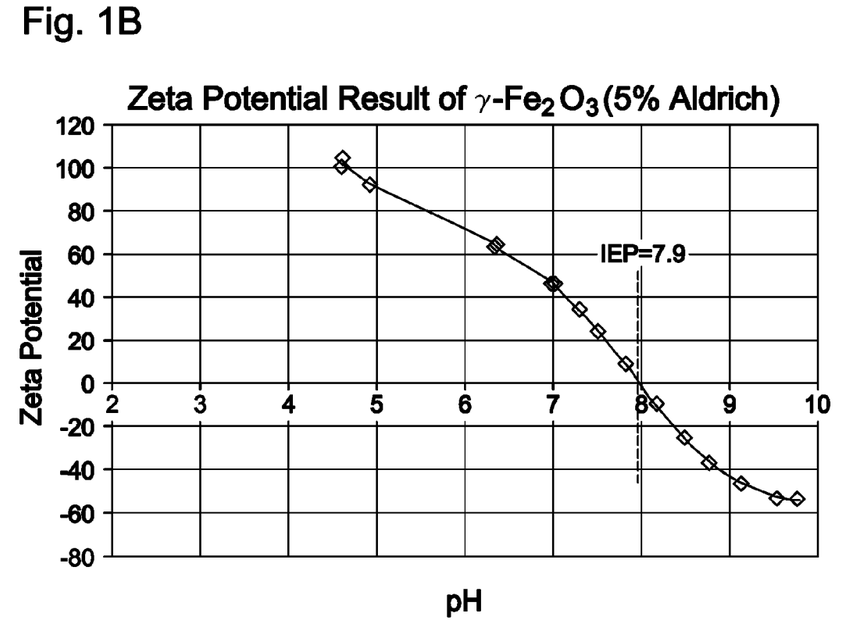
FIG. 1B also relates to Example 1 and shows that the $Fe_2O_3$ slurry has an isoelectric point (IEP) of 7.9.
Figure 1C:
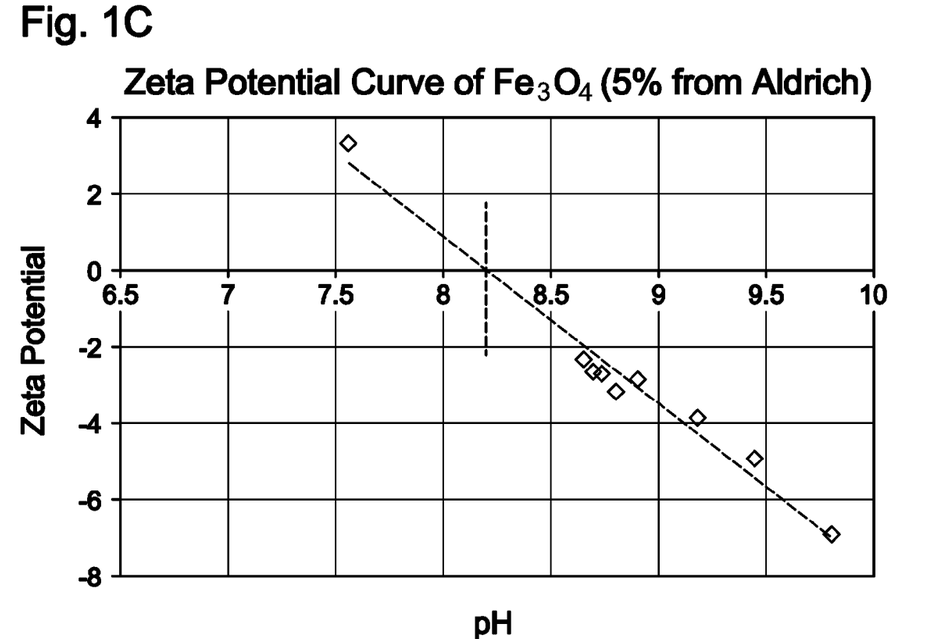
FIG. 1C also relates to Example 1 and shows that the $Fe_3O_4$ slurry has an isoelectric point (IEP) of 8.2.

FIG. 1A shows that the foulant has an isoelectric point (IEP) of 5.8; that is, the foulant is negatively charged at pH higher than 5.8 and positively charged at pH below 5.8. FIG. 1B shows that the $Fe_2O_3$ slurry has an isoelectric point (IEP) of 7.9; that is, the $Fe_2O_3$ particles are negatively charged at pH higher than 7.9 and positively charged at pH below 7.9. FIG. 1C shows that the $Fe_3O_4$ slurry has an isoelectric point (IEP) of 8.2; that is, the $Fe_3O_4$ particles are negatively charged at pH higher than 8.2 and positively charged at pH below 8.2. In all three cases, the further that the pH is away from the IEP, the higher the surface charge.

In order to show that the measurement of zeta potential of the foulant and the effective zeta potential of the metal surface could be used to predict where fouling could be greatly reduced, the pH of the condensed liquid stream of an oxygenate-to-olefin reaction was regulated in a pH range of 5 to 5.5 for a period 4 weeks. A cold finger of 316 stainless steel, cooled by water at a nominal temperature of 90° F. (32° C.), was inserted into the condensed liquid stream under process conditions at the start of the 4-week period, and when it was removed for observation at the conclusion of this period, it was found to have no significant fouling. As a comparison, an identical cold finger was inserted into the condensed liquid stream of an oxygen-to-olefin reaction for four weeks, but with no pH regulation. The average pH during the 4-week period was measured to be about 7. Other process conditions were held the same as during the period of pH regulation. When the cold finger was removed at the conclusion of the four-week period, heavy surface fouling was observed.

Example 2

Figure 2:
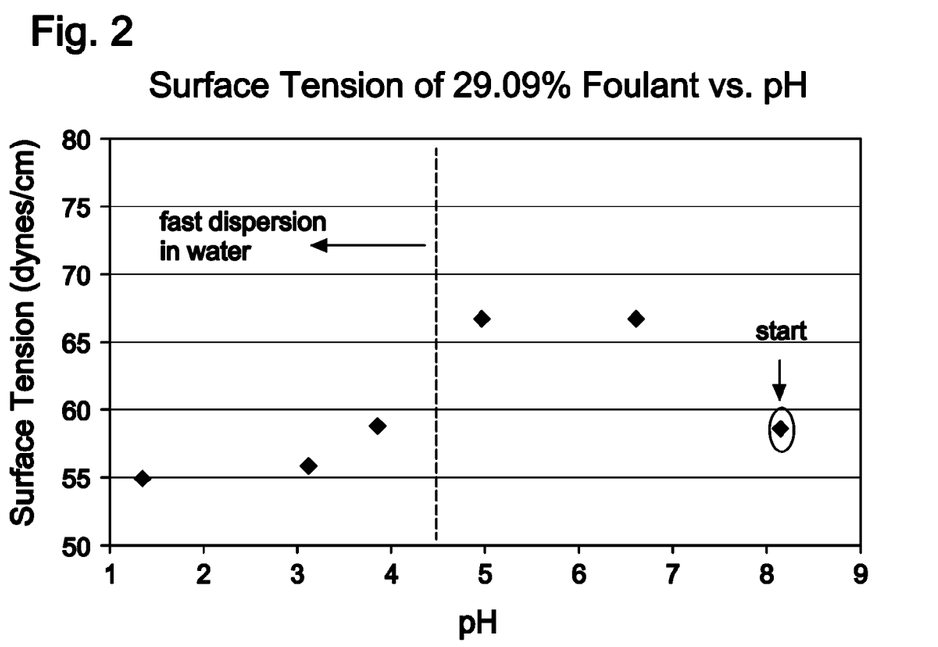
FIG. 2 is a plot of the surface tension as a function of pH corresponding to Example 2.

A slurry containing 29.09 wt % of the foulant used in Example 1 was made by diluting the foulant. The slurry had a pH of 8.14 and a surface tension of 58.7 dyne/cm measured using a CSC 70545 Tensiometer from CSC Scientific Co., Fairfax, Va. The pH of the slurry was lowered by adding a concentrated nitric acid solution in order to maintain the solid content nearly constant. Surface tension of the pH-adjusted samples was measured after each adjustment. Between measurements, the de Nouy (also cited occasionally as DuNouy or du Nouy) platinum-iridium ring from the tensiometer was brought into contact with de-ionized water to gauge the slurry's dispersion rate. The sample without pH adjustment dispersed slowly in water. There was a sudden change in dispersion rate when the pH of the slurry was reduced from 5 to 3.8. The results are provided in FIG. 2.

The point at which a fast dispersion is achieved corresponds to a state in which foulant no longer adheres to a metal surface. While not wishing to be bound, it is believed that this is the point where the zeta potential of the foulant in the condensed liquid stream of the oxygen-to-olefin reaction and the effective zeta potential of the equipment surface in contact with the condensed liquid stream are such that the foulant is not significantly attracted to the equipment surface by electro- or electro-diffusive forces as would otherwise be established by significant electric charge differences, chemical potential gradients, concentration gradients, and the like, either alone or acting in combination. As is known, surface tension measurement is one way to evaluate the strength of these effects. The transition to fast dispersion occurs at the transition from a negatively charged surface to a positively charged surface, as reflected in the zeta potential measurement. From FIG. 2, it can be seen that the change in surface charge corresponded to a change in the surface tension as pH was adjusted. As the pH was lowered from 8.1 to 5, the surface tension increased to its maximum around a pH of 5. A continuous reduction in surface tension was seen as the pH was lowered below 5. Therefore, a fast dispersion rate of the foulant slurry in water was achieved at a pH of around 5.

Example 3

Figure 3:
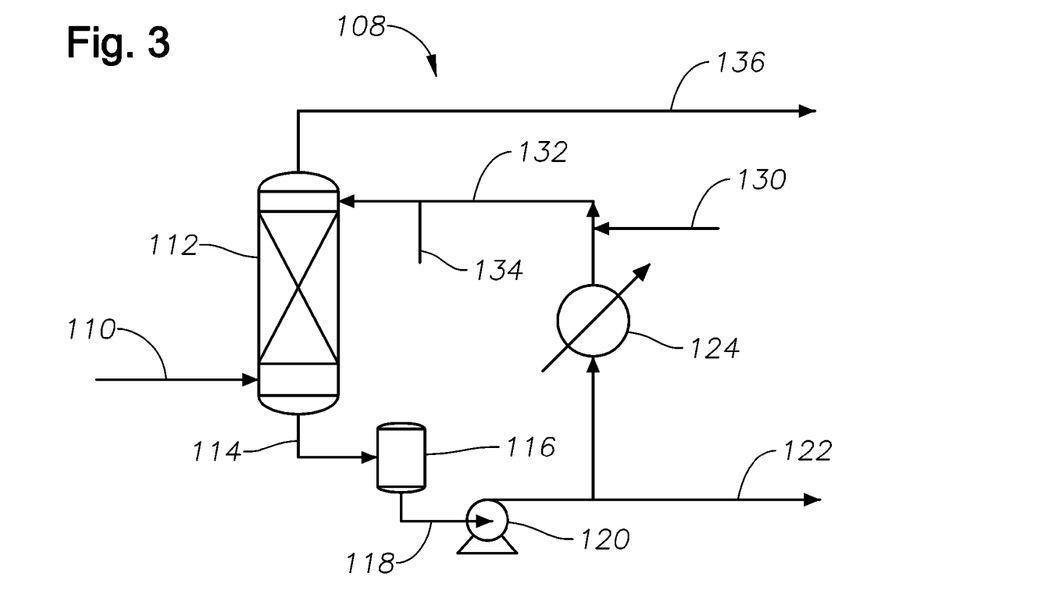
FIG. 3 shows schematically the conversion process of methanol vapor fed to a fluidized bed reactor containing a fluidized catalyst under conditions to convert 95% of the methanol to a composition comprising olefins, water, coke, organic acids, and catalyst fines.

Methanol vapor was fed to a fluidized bed reactor containing a fluidized SAPO-34 catalyst under conditions to convert 95% of the methanol to a composition comprising olefins, water, coke, organic acids, and catalyst fines. The conversion process is schematically shown in FIG. 3, in which reactor effluent is fed in line 110 to a quench system 108, where superheated vapor is cooled and water vapor and unreacted methanol are condensed. The quench system 108 includes a quench vessel 112, for example a packed column for direct contact heat transfer, a surge vessel 116, a centrifugal circulation pump 120, and a heat exchanger 124, such as a water-cooled heat exchanger. The condensed liquid, which is predominantly water with some oxygenated hydrocarbons, organic acids, and catalyst particles, are withdrawn from the bottom of the quench device 112 and recirculated through the water-cooled heat exchanger 124 to the top of the quench vessel 112 using the circulation pump 120. Cooled liquid quench medium 132 contacts the reactor effluent in line 110 in the quench vessel 112, where the gases are cooled, and the water and other oxygenates are condensed. A quench bottoms stream 114 is withdrawn from the quench vessel 112 and fed into the surge vessel 116. The net production of liquid is withdrawn from the pump discharge based on level in the surge vessel 116, and is sent to further processing for separation of oxygenated species from the water and catalyst particles 122. The ratio of liquid recirculated to that withdrawn is about 10:1. The olefin product vapors, and other light gases, exit the overhead of the quench device 112 as the quenched effluent stream 136 for further processing. Caustic soda in line 130 is injected into the quench medium 132 after the heat exchanger 124 in order to control the pH of the recirculated quench medium. The pH of the recirculated quench medium 132 is measured at 134.

Instrumentation on the pilot plant equipment allows monitoring of the flow rate and temperatures of the quench medium in and out of the shell side of the heat exchanger 124, as well as the inlet and outlet temperatures of the cooling water on the tube side of the heat exchanger 124. Using these data, calculation of the heat duty and log-mean temperature difference of the heat exchanger 124 can be performed by those skilled in the art. The surface area of the exchanger 124 is known, which allows a direct calculation of the heat transfer coefficient of the heat exchanger 124 according to the equation, $$U = \frac{Q}{A \cdot \Delta T_{lm}} \quad (1)$$

where U is the heat transfer coefficient based on outside tube area, Q is the duty, A is the outside surface area of the tubes, and $\Delta T_{lm}$ is the log-mean temperature difference driving force in the exchanger.

Figure 4:
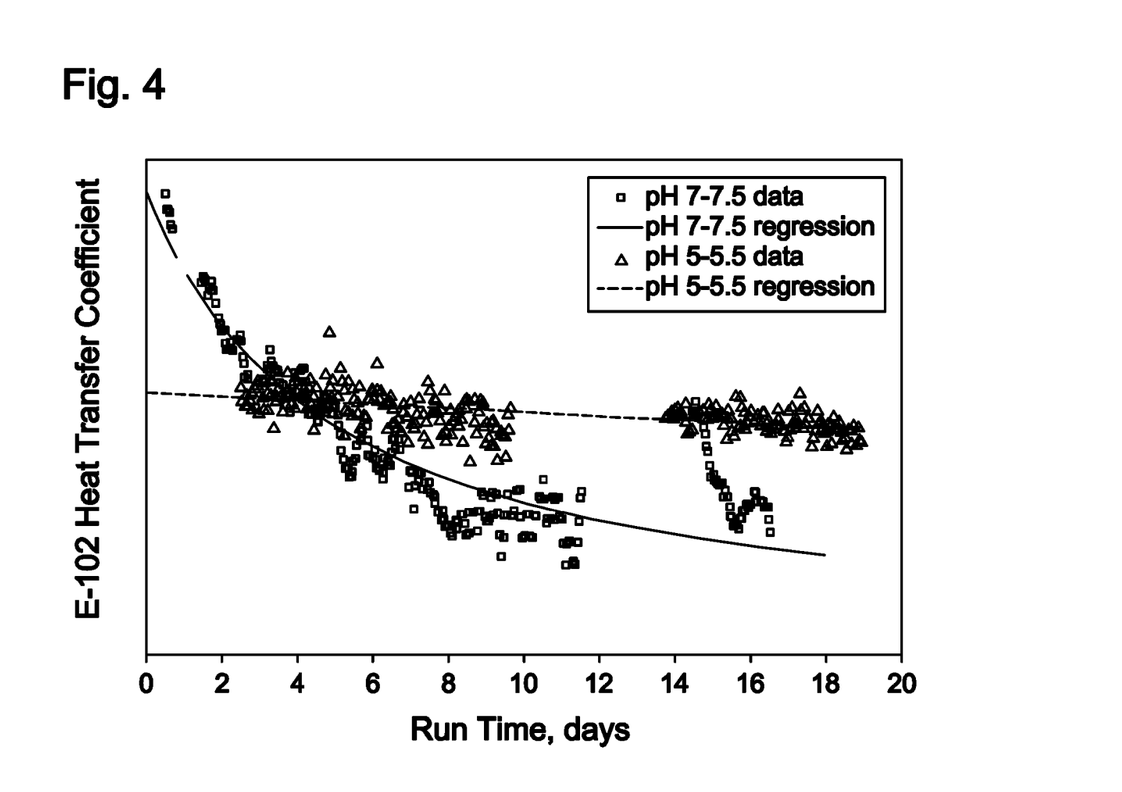
FIG. 4 represents the heat transfer coefficient versus run time since exchanger cleaning in the Examples.

Fouling of the heat exchanger 124 was monitored over time by analyzing the heat transfer coefficient data. The calculated heat transfer coefficient declined over time, indicating an accumulation of foulant on the heat transfer surfaces. The heat transfer coefficient is plotted versus time for two conditions in FIG. 4. It was found that the heat transfer coefficient data could be fit to the following equation, $$U(t) = \frac{1}{\frac{1}{U_0} + at} \quad (2)$$

where U(t) is the heat transfer coefficient over time, $U_o$ is the initial (clean) heat transfer coefficient, a is the fouling rate, and t is the time since the exchanger was cleaned.

FIG. 4 represents the heat transfer coefficient versus run time since exchanger cleaning. Example A was operated with a pH of 7-7.5, and Example B was operated with a pH of 5-5.5.

In Example A, caustic soda was injected at a rate sufficient to neutralize all of the organic acids, resulting in a pH of the cooled quench medium that ranged between 7 and 7.5. The heat transfer data for Example A is represented by the squares in FIG. 4. A regression of the fouling Equation (2) is represented by the solid line in FIG. 4. The best fit of the data was obtained with a fouling rate "a" of 0.000473 $ft^{2} \cdot °$ F./Btu (about 0.232 $cm^{2} \cdot °$ C./kJ).

In Example B, the exchanger was disassembled and thoroughly cleaned. The pilot plant was re-started, and caustic soda was injected at a rate that did not neutralize all of the organic acids but did control the pH of the cooled quench medium in the range of 5 to 5.5. The heat transfer data for Example B is represented by the triangles in FIG. 4. A regression of the fouling Equation (2) is represented by the dashed line in FIG. 4. The best fit of the data was obtained with a fouling rate "a" of 0.000033 $ft^{2} \cdot °$ F./Btu (about 0.016 $cm^{2} \cdot °$ C./kJ). This is a decrease in the fouling rate of more than 10-fold compared with the fouling rate observed in Example A.

The principles and modes of operation of this invention have been described above with reference to various exemplary and preferred embodiments. As understood by those of skill in the art, the overall invention, as defined by the claims, encompasses other preferred embodiments not specifically enumerated herein.

What is claimed:

1. A method for forming and separating an olefin fraction which comprises the following steps:
   i) contacting oxygenate with a zeolitic aluminosilicate molecular sieve catalyst to form an olefin stream;
   ii) cooling the olefin stream in a quench system to form a first fraction comprising olefin and a second fraction comprising condensed water and entrained catalyst, wherein the quench system is comprised of a surface structure and at least a portion of the surface structure contacts the condensed water;
   iii) injecting an antifouling agent into the quench system in an amount to control a zeta potential of the entrained catalyst in the second fraction and an effective zeta potential of the surface of the quench system contacting the condensed water both in a positive range or both in a negative range within an absolute value of at least 2 mV; and
   iv) separating at least a portion of the second fraction from the first fraction.

2. The method of claim 1, wherein the quench system comprises at least one quench vessel and a pumparound system in fluid connection with the quench vessel.

3. The method of claim 2, wherein the antifouling agent is injected into the quench vessel, the pumparound system or both.

4. A method for separating water and entrained solids from an olefin stream which comprises the following steps:
   i) cooling the olefin stream in a quench system to form a first fraction comprising olefin and a second fraction comprising condensed water and entrained solids comprising a zeolitic aluminosilicate molecular sieve catalyst, wherein the quench system is comprised of a surface structure and at least a portion of the surface structure contacts the condensed water;
   ii) injecting an antifouling agent into the quench system in an amount to control a zeta potential of the entrained solids in the second fraction and an effective zeta potential of the surface of the quench system contacting the condensed water both in a positive range or both in a negative range within an absolute value of at least 2 mV; and
   iii) separating at least a portion of the second fraction from the first fraction.

5. The method of claim 4, wherein the zeolitic aluminosilicate molecular sieve catalyst comprises particles containing alumina and silica present in a silica to alumina (Si:$Al_2$) ratio of at least about 100.

6. The method of claim 4, wherein the olefin stream is provided from a unit in which oxygenate is contacted with the zeolitic aluminophosphate molecular sieve catalyst to form the olefin stream.

* * * * *